United States Patent [19]

Tanno et al.

[11] Patent Number: 5,753,281
[45] Date of Patent: May 19, 1998

[54] METHOD OF PREPARING A SYNTHETIC BUTTER FLAVOR

[75] Inventors: Katsutoshi Tanno, Saitama; Kenji Ganmyo; Nobuyuki Kawai, both of Tokyo; Tetsuo Nakamura, Saitama, all of Japan

[73] Assignee: Snow Brand Milk Products Co., Ltd., Hokkaido, Japan

[21] Appl. No.: 722,636

[22] Filed: Sep. 27, 1996

[30] Foreign Application Priority Data

Sep. 29, 1995 [JP] Japan ................................ 7-252147

[51] Int. Cl.⁶ .................................................. A23C 9/12
[52] U.S. Cl. ...................... 426/35; 426/34; 426/533; 426/534; 426/650
[58] Field of Search ........................ 426/35, 34, 533, 426/534, 650, 42, 580, 586, 663, 664

[56] References Cited

U.S. PATENT DOCUMENTS 4,996,069  2/1991  de Hey et al. ........................ 426/248

OTHER PUBLICATIONS

Nozawa et al. Patent Abstracts of Japan, Abstracting JP 57-206343, Dec. 1982.

Shiyukunobe et al., Patent Abstracts of Japan, Abstracting JP 63-240755, Oct. 1988.

Tojo et al., Patent Abstracts of Japan, Abstracting JP 05-91851, Apr. 1993.

Tojo et al., Patent Abstracts of Japan, Abstracting JP 06-125733, Apr. 1994.

*Primary Examiner*—Leslie Wong
*Attorney, Agent, or Firm*—Townsend & Banta

[57] ABSTRACT

A method of preparing a synthetic butter flavor having enriched milk flavor and butter flavor, containing the steps of hydrolysing a milk fat with a lipolytic enzyme and then oxidizing the hydrolysate of the milk fat by ultraviolet irradiation. The hydrolysate of the milk fat is preferably oxidized by ultraviolet irradiation to have a POV of 1.5 to 9.0, in particular 4.0 to 7.5.

7 Claims, No Drawings

METHOD OF PREPARING A SYNTHETIC BUTTER FLAVOR

BACKGROUND OF THE INVENTION

1. Field of the Invention

The present invention relates to a method of preparing a synthetic butter flavor having enriched milk flavor and butter flavor.

2. Description of Background and Related Art

Many methods of preparing synthetic butter flavors comprising acting lipolytic enzyme such as lipase or esterase on milk fats such as creams or butter fats have been reported, and the techniques have been practically used However, the synthetic butter flavors obtained by the methods could not be free from the accompaniment of stimulus rancid odor produced by the enzymic lipolysis and of undesirable oily taste derived from middle fatty acids and higher fatty acids, so that all the synthetic butter flavors had disadvantages of having poor delicate aroma balance, favorable milk flavor and butter flavor of natural butter.

On the other hand, it has been known that flavor of butter fat is changed by means of oxidation by means such as heating. In addition, it has also been known that the flavor equivalent to that of natural butter may be given to foods by adding an oxidized butter fat to the foods (Japanese Patent Laid-Open Publication No.1-39962).

Accordingly, it is an object of the present invention to provide a method of preparing a synthetic butter flavor which has enriched milk flavor and butter flavor and has inhibited stimulus rancid odor and which is very similar to the flavor of natural butter.

SUMMARY OF THE INVENTION

The present inventors have researched earnestly in order to improve the synthetic butter flavor obtained from the conventional enzymic lipolysis, with taking notice of the change of flavor due to the oxidation of butter fat. As the results, they found that a synthetic butter flavor which is more similar to the flavor of natural butter and whose milk flavor and butter flavor are enriched and whose stimulus rancid odor is inhibited, can be prepared by hydrolyzing a butter fat with a lipolytic enzyme such as lipase and then oxidizing the hydrolysate by ultraviolet irradiation.

Thus the present invention provides a method of preparing a synthetic butter flavor having enriched milk flavor and butter flavor comprising the steps of hydrolyzing a milk fat with a lipolytic enzyme and then oxidizing the hydrolysate of the milk fat by ultraviolet irradiation.

The present invention will be explained in detail.

First, with the method of preparing a synthetic butter flavor of the present invention, the hydrolysis of a milk fat is carried out by acting a lipolytic enzyme on the milk fat. As the milk fat which may be used in the present invention, a variety of creams, butters and butter oils may be exemplified. These milk fats may be used alone or in combination with any other milk fat. Preferably, the milk fat used as a raw material for the synthetic butter flavor is heated to sterilize at 80° to 130° C. for 10 to 60 min, and then cooled down to a temperature suitable for an enzyme reaction. Water may be added to the milk fat in advance, and then an emulsifying agent such as lecithin, glycerin fatty acid ester, sucrose fatty acid ester may be added.

As the lipolytic enzyme which may be used in the present invention, a lipolytic enzyme obtained from swine pancreas or mouth secretory of infant domestic animals, and a lipolytic enzyme produced by a microorganism belonging to a genus such as Penicillium genus, Chromobacterium genus, Aspergillus genus, Mucor genus, Candida genus or Pseudomonas genus may be exemplified. These lipolytic enzyme may be used alone or in combination with any other lipolytic enzyme. Preferably, the lipolytic enzyme may be dissolved in water and added or may be added to the raw milk fat directly so as to have an added amount of the enzyme of 0.005 to 5 weight% per the raw milk fat. Then an enzyme reaction is preferably carried out at a temperature suitable for the enzymic reaction, e.g., 25° to 60° C. for 1 to 120 hours. Preferably, after completion of the reaction, the enzyme is deactivated by heating it at 80° to 100° C. for 10 to 90 min., and the hydrolysate of the milk fat is sterilized at the same time.

Then, with the method of the present invention, the hydrolysate of the milk fat is oxidized by ultraviolet irradiation. The ultraviolet irradiation may be carried out using a generally used ultraviolet lamp, such as low-pressure ultraviolet lamp or high-pressure ultraviolet lamp. As an ultraviolet irradiation method, ultraviolet may be irradiated from the upper side of the hydrolysate of the milk fat, but if an object oxide is obtained in a short time, ultraviolet may be irradiated by immersing an ultraviolet lamp into the hydrolysate of the milk fat. Further, if the ultraviolet irradiation on the hydrolysate of the milk fat is carried out with stirring, a large amount of the hydrolysate of the milk fat may be oxidized in a high efficiency.

As an characteristic of the oxidation of the hydrolysate of the milk fat by ultraviolet irradiation, a Peroxide Value (POV) which is generally used as a characteristic of fat oxidation, may be used. The POV is determined according to the Standard Oil and Fat Analytical Test Method No.2.4. 12-71 established by Japan Oil Chemical Institute. With the present invention, the ultraviolet irradiation is stopped when the POV of the hydrolysate of the milk fat of 1.5 to 9.0, preferably 4.0 to 7.5, is obtained. In general, when the ultraviolet irradiation is carried out on the hydrolysate of the milk fat with stirring at 35° to 60° C., an object POV may be obtained in 24 to 100 hours.

DESCRIPTION OF THE PREFERRED EMBODIMENTS

The present invention will be described in detail with reference to the following preferred embodiment.

First, a lipolytic enzyme obtained from swine pancreas or mouth secretory of infant domestic animals, or a lipolytic enzyme produced by a microorganism belonging to a genus such as Penicillium genus, Chromobacterium genus, Aspergillus genus, Mucor genus, Candida genus or Pseudomonas genus is acted on a milk fat such as creams, butters or butter oils in order to hydrolyze the milk fat. Then ultraviolet irradiation is carried out on the resulted hydrolysate of the milk fat so as to oxidize the hydrolysate until a POV of 1.5 to 9.0, preferably 4.0 to 7.5 is obtained. By the treatment, a synthetic butter flavor having enriched milk flavor and butter flavor and having inhibited stimulus rancid odor may be prepared.

The synthetic butter flavor of the present invention having enriched milk flavor and butter flavor and having excellent favorabilities, may be compounded in an oil and fat such as margarine, shortening or butter, a frozen desert such as ice cream, ice milk, lacto ice or soft cream, a fermented milk product such as yoghurt or lactic acid beverage, or a confectionery such as biscuits or cookies so as to provide milk flavor and butter flavor to the foods.

EXAMPLES

The present invention will be described in detail by reference to the following Examples. The Examples should not, however, be construed as limiting the scope of the invention.

Example 1

Unsalted butter was dissolved at 40° to 80° C., and centrifuged (50000 rpm, 10 min.) to obtain 100 g of butter fat. 100 g of the butter fat was heated at 80° C. for 10 min. to sterilize, and then cooled down to 50° C. To the butter fat, 0.01 g of a lipolytic enzyme produced by a Pseudomonas Genus microorganism (Lipase P; manufactured by Amano Pharmaceutical Co.,Ltd.) dissolved in 3 g of water, was added. An enzyme reaction was carried out at 50° C. for 18 hours with stirring, and then the enzyme was deactivated by heating at 100° C. for 60 min. to complete the enzyme reaction. Then it was centrifuged (5000 rpm, 10 min.) to remove water content, and approximately 100 g of hydrolysate of the butter fat having an acid value (AV) of 50 was prepared. The POV of the hydrolysate of the butter fat was 0.8.

Then ultraviolet irradiation was carried out on 100 g of the hydrolysate of the butter fat at 45° C. using a photochemical reaction device (manufactured by Shigemi Standard Co., Ltd.). The ultraviolet irradiation was made using a low-pressure mercury lamp of 13W (manufactured by Shigemi Standard Co.,Ltd.), with stirring. The following trial products No.1 to 19 of synthetic butter flavor having different POVs were prepared.

Trial Product No.1: POV 1.0
Trial Product No.2: POV 1.5
Trial Product No.3: POV 2.0
Trial Product No.4: POV 2.5
Trial Product No.5: POV 3.0
Trial Product No.6: POV 3.5
Trial Product No.7: POV 4.0
Trial Product No.8: POV 4.5
Trial Product No.9: POV 5.0
Trial Product No.10: POV 5.5
Trial Product No.11: POV 6.0
Trial Product No.12: POV 6.5
Trial Product No.13: POV 7.0
Trial Product No.14: POV 7.5
Trial Product No.15: POV 8.0
Trial Product No.16: POV 8.5
Trial Product No.17: POV 9.0
Trial Product No.18: POV 9.5
Trial Product No.19: POV 10.0

Comparative Example 1

Unsalted butter was dissolved at 40° to 80° C., and centrifuged (5000 rpm, 10 min.) to obtain 100 g of butter fat. 100 g of the butter fat was heated at 80° C. for 10 min. to sterilize, and then cooled down to 50° C. To the butter fat, 0.01 g of a lipolytic enzyme produced by a Pseudomonas Genus microorganism (Lipase P; manufactured by Amano Pharmaceutical Co.,Ltd.) dissolved in 3 g of water, was added. An enzyme reaction was carried out at 50° C. for 18 hours with stirring, and then the enzyme was deactivated by heating at 100° C. for 60 min. to complete the enzyme reaction. Then it was centrifuged (5000 rpm, 10 min.) to remove water content, and approximately 100 g of hydrolysate of the butter fat having an acid value (AV) of 50 was prepared. The POV of the hydrolysate of the butter fat was 0.8. The ultraviolet irradiation was not carried out.

Test Example 1

To a cookie dough in which 400g of shortening, 200 g of granulated-sugar, 100 g of whole egg and 600 g of flour were compounded, each 0.12 g of the synthetic butter flavor obtained from Example 1 and Comparative Example 1 was added per 100 g of the cookie dough. The cookie dough was baked at 180° C. for 10 min. to prepare cookie. An organoleptic evaluation was carried out on the cookie by 20 well-trained panels. The results were shown in Table 1.

TABLE 1

| Example 1 | Milk flavor | Butter flavor |
|---|---|---|
| Trial Product No. 1 | = | = |
| Trial Product No. 2 | △ | = |
| Trial Product No. 3 | △ | = |
| Trial Product No. 4 | △ | △ |
| Trial Product No. 5 | ○ | △ |
| Trial Product No. 6 | ○ | △ |
| Trial Product No. 7 | ○ | ○ |
| Trial Product No. 8 | ○ | ○ |
| Trial Product No. 9 | ◎ | ○ |
| Trial Product No. 10 | ◎ | ○ |
| Trial Product No. 11 | ◎ | ○ |
| Trial Product No. 12 | ◎ | ◎ |
| Trial Product No. 13 | ○ | ◎ |
| Trial Product No. 14 | ○ | ◎ |
| Trial Product No. 15 | △ | ○ |
| Trial Product No. 16 | △ | △ |
| Trial Product No. 17 | = | △ |
| Trial Product No. 18 | X | = |
| Trial Product No. 19 | X | = |

The organoleptic evaluation was made according to the following five standards.

◎: much more excellent than Comparative Example 1
○: more excellent than Comparative Example 1
△: slightly more excellent than Comparative Example 1
=: equivalent to Comparative Example 1
X: inferior to Comparative Example 1

These results show that the synthetic butter flavor having the POV of 1.5 to 9.0, in particular 4.0 to 7.5, are more excellent in both milk flavor and butter flavor than the synthetic butter flavor obtained from Comparative Example 1.

As described above, the synthetic butter flavor which has enriched milk flavor and butter flavor and whose stimulus rancid odor is inhibited compared to the conventional synthetic butter flavor, may be prepared by oxidizing the hydrolysate of the milk fat obtained by acting a lipolytic enzyme to the milk fat by ultraviolet irradiation.

What is claimed is:

1. A method of preparing a synthetic butter flavor having enriched milk flavor and butter flavor comprising the steps of hydrolysing a milk fat with lipase and then oxidizing the hydrolysate of the milk fat by ultraviolet radiation,
    wherein the hydrolysate of the milk fat is oxidized by ultraviolet radiation to have a peroxide value (POV) of 1.5 to 9.0.

2. A method of preparing a synthetic butter flavor according to claim 1, wherein the hydrolysate of the milk fat is oxidized by ultraviolet irradiation to have a POV of 4.0 to 7.5.

3. A method of preparing a synthetic butter flavor according to claim 1, wherein the lipase is used in an amount of 0.005 to 5 weight% per the milk fat.

4. A method of preparing a synthetic butter flavor according to claim 1, wherein the ultraviolet irradiation is carried out with stirring.

5. A method of preparing a synthetic butter flavor according to claim 1, wherein the milk fat is creams, butters or butter oils.

6. A method of preparing a synthetic butter flavor according to claim 1, wherein the lipase is obtained from swine pancreas or mouth secretory of infant domestic animals, or lipase produced by a Penicillium genus, Chromobacterium genus, Aspergillus genus, Mucor genus, Candida genus or Pseudomonas genus microorganism.

7. A method of preparing a synthetic butter flavor according to claim 1, wherein the ultraviolet irradiation is carried out by immersing an ultraviolet lamp into the hydrolysate of the milk fat.

* * * * *